United States Patent
Shim et al.

(10) Patent No.: US 8,632,969 B2
(45) Date of Patent: Jan. 21, 2014

(54) METHOD AND A DEVICE FOR DETECTING GENES

(75) Inventors: Jeo Young Shim, Yongin-si (KR); Jung Im Han, Yongin-si (KR); Won Seok Chung, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 402 days.

(21) Appl. No.: 12/141,448

(22) Filed: Jun. 18, 2008

(65) Prior Publication Data

US 2009/0090175 A1    Apr. 9, 2009

(30) Foreign Application Priority Data

Oct. 9, 2007    (KR) .................. 10-2007-0101700

(51) Int. Cl.
| C12Q 1/68 | (2006.01) |
| C12P 19/34 | (2006.01) |
| C12M 1/34 | (2006.01) |
| C12M 3/00 | (2006.01) |
| H01L 21/70 | (2006.01) |
| G01N 15/06 | (2006.01) |
| G01N 27/00 | (2006.01) |
| C07H 21/02 | (2006.01) |
| C07H 21/04 | (2006.01) |

(52) U.S. Cl.
USPC ......... 435/6.1; 435/6.12; 435/91.1; 435/91.2; 435/287.2; 435/287.8; 435/287.9; 257/368; 422/68.1; 422/82.01; 536/23.1; 536/24.33

(58) Field of Classification Search
USPC ......... 435/6.1, 6.12, 91.1, 91.2, 287.2, 287.8, 435/287.9; 257/368; 422/68.1, 82.01; 536/23.1, 24.33
See application file for complete search history.

(56) References Cited

U.S. PATENT DOCUMENTS

| 4,238,757 A | 12/1980 | Schenck |
| 4,777,019 A | 10/1988 | Dandekar |
| 4,960,722 A | 10/1990 | Ogawa |
| 5,160,597 A | 11/1992 | Colapicchioni et al. |

(Continued)

FOREIGN PATENT DOCUMENTS

| JP | 2003 322633 | 11/2003 |
| JP | 2004 004007 | 1/2004 |
| JP | 2006084417 | 3/2006 |
| WO | 2005 121765 A1 | 12/2005 |

OTHER PUBLICATIONS

JP2007-139762A [Claim], MT—printed on Sep. 15, 2012, pp. 1-2.*

(Continued)

*Primary Examiner* — Narayan Bhat
(74) *Attorney, Agent, or Firm* — Cantor Colburn LLP

(57) ABSTRACT

A method and a device for detecting nucleic acid are disclosed, wherein impurities in a sample can be easily removed. The method comprises injecting a sample containing an adsorption medium with nucleic adsorbed thereon into a chamber; washing the sample; heating the sample to denature the nucleic acid; cooling down; and detecting nucleic acid by using the biomolecule detection device. The device includes: a source and a drain region; a gate electrode layer; a chamber formed over the semiconductor substrate including the gate electrode layer; and a heating means, wherein a gate adsorption layer to which a nucleic acid is adsorbed is formed on the gate electrode layer. A single-stranded nucleic acid is adsorbed to the gate adsorption layer, and a channel is formed between the source and the drain region. The current in the channel provides a basis to detect a gene.

14 Claims, 7 Drawing Sheets

(56) References Cited

U.S. PATENT DOCUMENTS

| | | | |
|---|---|---|---|
| 5,466,348 | A | 11/1995 | Holm-Kennedy |
| 6,210,977 | B1 | 4/2001 | Sieben et al. |
| 6,436,647 | B1 | 8/2002 | Quate et al. |
| 6,914,279 | B2 | 7/2005 | Lu et al. |
| 2002/0006632 | A1 | 1/2002 | Ponnampalam et al. |
| 2002/0024099 | A1* | 2/2002 | Watanabe et al. ............. 257/368 |
| 2002/0117659 | A1 | 8/2002 | Lieber et al. |
| 2003/0073071 | A1 | 4/2003 | Fritz et al. |
| 2004/0086867 | A1* | 5/2004 | Han ................................. 435/6 |
| 2004/0121354 | A1* | 6/2004 | Yazawa et al. .................... 435/6 |
| 2004/0195563 | A1 | 10/2004 | Bao et al. |
| 2005/0040483 | A1 | 2/2005 | Offenhauser et al. |
| 2005/0247961 | A1 | 11/2005 | Zhou |
| 2006/0141474 | A1* | 6/2006 | Miyahara et al. ................. 435/6 |
| 2006/0197118 | A1 | 9/2006 | Migliorato et al. |
| 2006/0246443 | A1 | 11/2006 | Bockelmann et al. |
| 2007/0059741 | A1* | 3/2007 | Kamahori et al. ................ 435/6 |
| 2007/0207471 | A1* | 9/2007 | Osaka et al. ....................... 435/6 |
| 2007/0248958 | A1* | 10/2007 | Jovanovich et al. ............. 435/6 |
| 2009/0153130 | A1* | 6/2009 | Shim et al. ....................... 324/72 |

OTHER PUBLICATIONS

JP2007-139762A [Description of Drawings], MT, printed on Sep. 15, 2012, p. 1.*

JP2007-139762A [Detailed Description], MT, printed on Sep. 15, 2012, pp. 1-12.*

JP2007-139762A [Drawings], MT, printed on Sep. 15, 2012, pp. 1-5.*

JP2007-139762A [Effect of the Invention], MT, printed on Sep. 15, 2012, p. 1.*

JP2007-139762A [Example], MT, printed on Sep. 15, 2012, pp. 1-4.*

JP2007-139762A [Means], MT, printed on Sep. 15, 2012, pp. 1-4.*

JP2007-139762A [Abstract With Publishing Date], MT, printed on Sep. 15, 2012, p. 1.*

JP2007-139762A [Technical Problem], MT, printed on Sep. 15, 2012, pp. 1-2.*

Bockelmann, Detecting DNA by field effect transistor arrays, Very Large Scale Integration, 2006 IFIP International Conference, 2006, pp. 161-165, Date of Conference: Oct. 16-18, 2006.*

Bockelmann, paper for establishing the date of publication, printed on Jul. 16, 2013, p. 1.*

Hytonen, Vesa P., et al., Chicken Avidin-related Protein 4/5 Shows Superior Thermal Stability when Compared with Avidin while Retaining High Affinity to Biotin, The Journal of Biological Chemistry, vol. 279, No. 10, Issue Mar. 5, pp. 9337-9343, 2004.

Gonzalez, Martin, et al., Interaction of Biotin with Streptavidin, Thermostability and Conformational Changes Upon Binding, The Journal of Biological Chemistry, vol. 272, No. 17, Issue of Apr. 25, pp. 11288-11294, 1997.

Johnson Hou, Chih-Sheng, et al., Label-Free Microelectronic PCR Quantification, Analytical Chemistry, vol. 78, No. 8, pp. 2526-2531, Apr. 15, 2006.

\* cited by examiner

Fig.2A
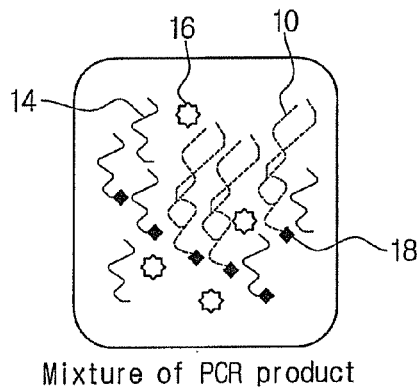
Mixture of PCR product
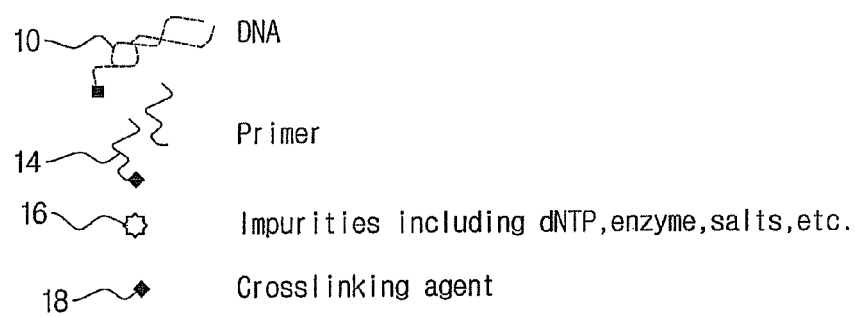
Fig.2B
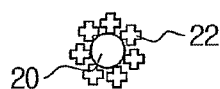
Fig.2C
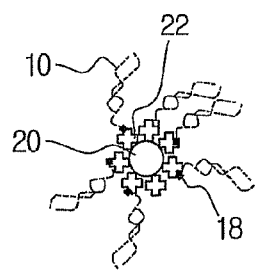

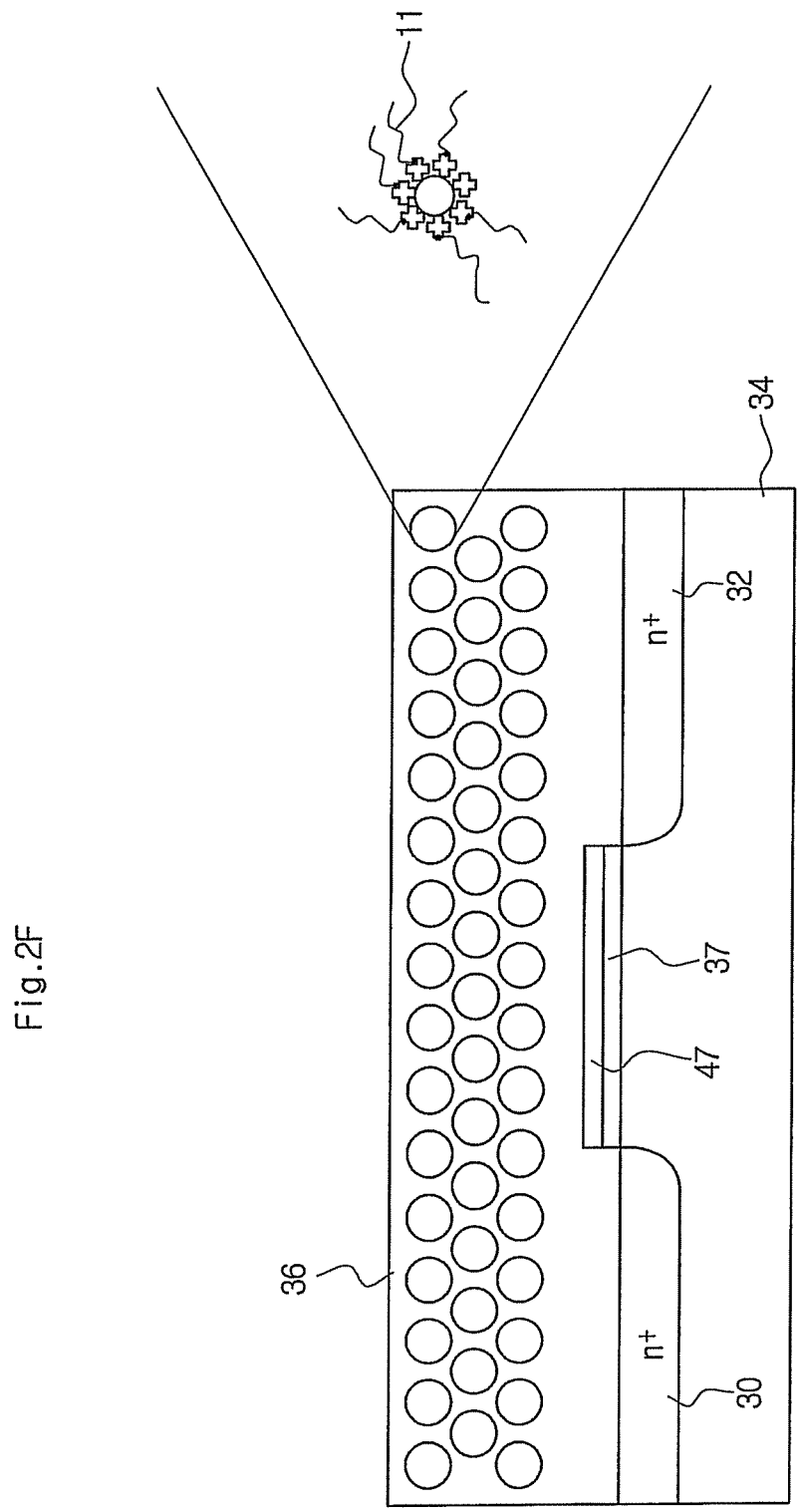

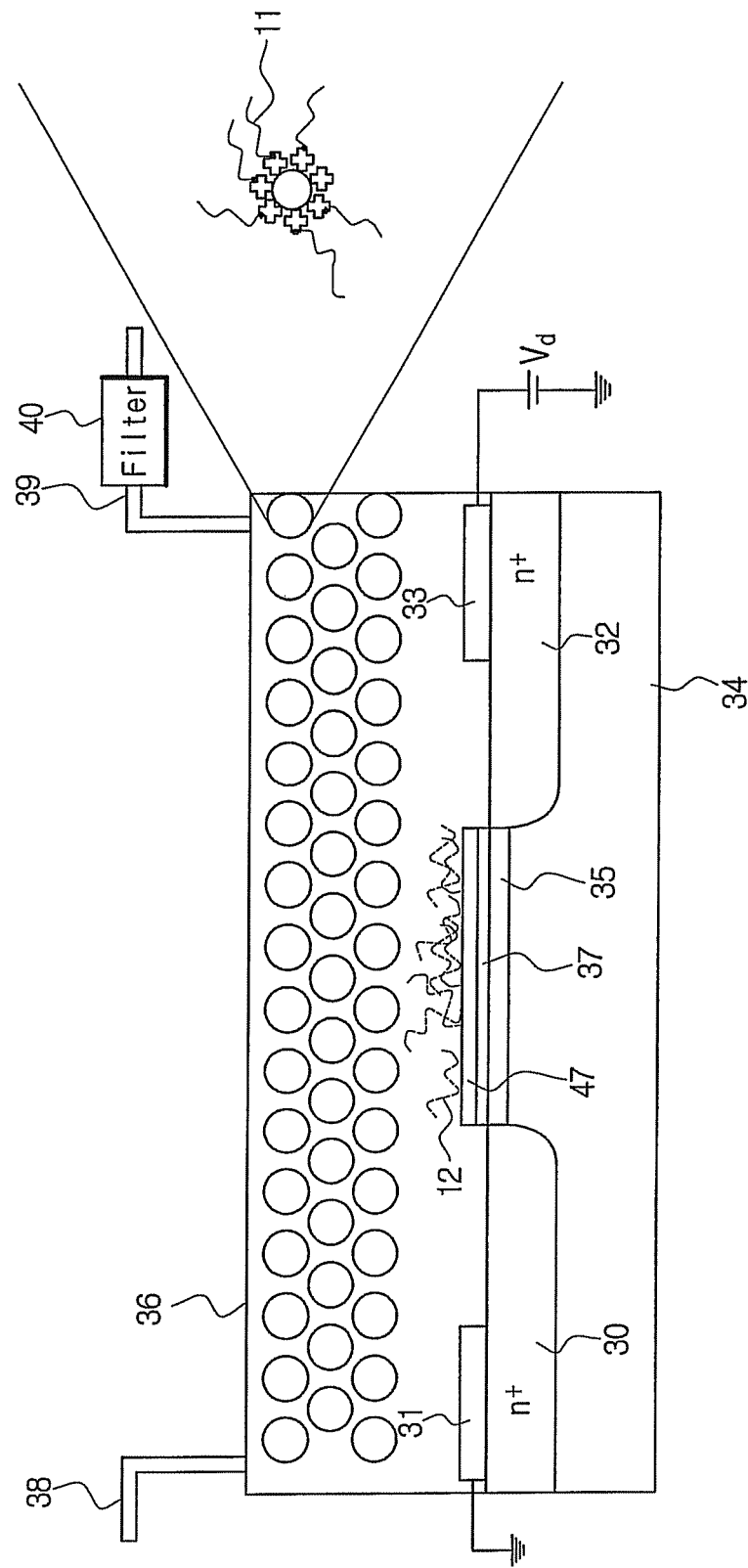

METHOD AND A DEVICE FOR DETECTING GENES

This application claims priority to Korean patent application No. 10-2007-0101700, filed on Oct. 9, 2007, the contents of which in its entirety are herein incorporated by reference.

BACKGROUND OF THE INVENTION

1. Field of the Invention

The present invention relates to a method and a device for detecting a nucleic acid such as DNA. More specifically, the present invention relates to a method and a device for detecting a nucleic acid by removing impurities that are produced in a PCR amplification process of a nucleic acid sample, denaturing the nucleic acid sample by heating, and adsorbing a single-stranded nucleic acid fragment prepared by denaturation onto a gate adsorption layer of a FET-based sensor.

2. Description of the Related Art

Among the many devices used for detecting nucleic acid, including DNAs, RNAs, PNAs (peptide nucleic acids), and other biomolecules, etc., with an electric signal, researches are now actively progressing to develop a transistor-based sensor. Researches are now actively progressing to develop a transistor-based sensor since these can be easily manufactured using a semiconductor process incorporated with an integrated circuit and MEMS (microelectromechanical system) fabrication process. Another advantage of the transistor-based sensor is that it can promptly provide a sensing result through an electrical signal processing.

The most well-known transistor-based sensor used to observe biological processes is a FET-based sensor employing a field-effect transistor (FET). The FET-based sensor is a small scale device, which can be advantageously used for a lab-on-a-chip (LOC) (which spots or diagnoses all types of diseases at once on a small chip), point of care (POC) and on the like testing methods.

A conventional FET-based sensor measures the surface charge density for use in measuring an electrical signal upon a target biomolecule that is adsorbed onto a gate surface.

In order to detect a biomolecule with the FET-based sensor, it is important to prepare a highly pure biomolecule sample. In other words, all impurities in the sample must be removed as much as possible.

For instance, a target nucleic acid for detection normally undergoes an amplification process, such as, for example, polymerase chain reaction (PCR), ligase chain reaction (LCR) and rolling circle amplification (RCA). Such amplification methods generally require the use of a variety of chemicals, e.g., enzymes, salts or monomers for polymerization, which naturally enter a sample during the reaction. These chemical impurities generally have an electric charge and can interfere with the FET-based sensor. Specifically, these chemical impurities can generate unwanted electric noises when nucleic acid in the sample are being detected through the FET-based sensor.

In one attempt to solve the above problem, a PCR product purification kit (from Qiagen) has been developed and is now commercially available. However, the purification kit, and other PCR purification kits, include a chaotropic salt. Therefore, no matter how efficiently impurities like enzymes, dNTP, or primers are removed from a PCR product through the purification kit, the purified sample including an amplified nucleic acid will still contain a considerable amount of the chaotropic salt.

Therefore, if the purification process was carried out in the presence of a chaotropic salt, it is necessary to lower the concentration of the salt by dialysis.

BRIEF SUMMARY OF THE INVENTION

The present invention provides a new method and device for detecting a nucleic acid where an adsorption medium, such as beads, adsorbs a nucleic acid (for example, DNA, RNA, or PNA, etc.) amplified by PCR, etc., and the nucleic acid is washed, and denatured by heating to produce a single-stranded nucleic acid that is later adsorbed onto a gate electrode of a FET-based sensor. According to an embodiment, when a single-stranded nucleic acid that is adsorbed onto a gate electrode of a FET-based sensor, the FET-based sensor detects the presence of a nucleic acid or its concentration by measuring current flowing through a channel formed between a source region and a drain region thereof.

It is a further object of the present invention to provide a method and a device for detecting a gene (e.g., DNA).

In one embodiment, the invention provides a method for detecting a nucleic acid, comprising injecting a sample containing an adsorption medium with a nucleic acid adsorbed thereon into a chamber of a biomolecule detection device; washing the sample in the chamber to remove impurities; heating the sample to denature the nucleic acid; cooling down the sample; and detecting a nucleic acid in the sample by using the biomolecule detection device.

In one embodiment, the invention provides a method for detecting a nucleic acid, comprising injecting a sample containing an adsorption medium with a nucleic acid adsorbed thereon into a chamber of a biomolecule detection device; washing the sample in the chamber to remove impurities; heating the sample to denature the nucleic acid; cooling down the sample; and detecting a nucleic acid in the sample by using the biomolecule detection device, wherein the biomolecule detection device comprises a source region and a drain region disposed apart from each other on a semiconductor substrate; a gate electrode layer formed between the source region and the drain region; and a chamber formed over the semiconductor substrate including the gate electrode layer, wherein the chamber can be used as a space for accommodating a nucleic acid-containing sample, wherein a gate adsorption layer to which a nucleic acid is adsorbed is formed at an upper portion of the gate electrode layer.

In another embodiment, the invention provides a method for detecting a nucleic acid, comprising washing a sample containing an adsorption medium with a nucleic acid adsorbed thereon to remove impurities; injecting the washed sample into a chamber of a biomolecule detection device; heating the sample to denature the nucleic acid; cooling down the sample; and detecting a nucleic acid in the sample by using the biomolecule detection device.

In another embodiment, the invention provides a device for detecting a nucleic acid, comprising a source region and a drain region disposed apart from each other on a semiconductor substrate; a gate electrode layer formed between the source region and the drain region; a chamber formed over the semiconductor substrate including the gate electrode layer, wherein the chamber can be used as a space for accommodating a nucleic acid-containing sample; and a heating means for heating the sample in the chamber, wherein a gate adsorption layer to which a nucleic acid is adsorbed is formed at an upper portion of the gate electrode layer.

When a gene is adsorbed onto the gate adsorption layer in the nucleic acid detection device according to the present invention, a channel is formed between the source region and the drain region, and current flowing through the channel is measured for use in the detection of nucleic acids in the sample.

The other objectives and advantages of the invention will be understood by the following description and will also be appreciated by the embodiments of the invention more clearly. Further, the objectives and advantages of the invention will readily be seen that they can be realized by the means and its combination specified in the claims.

BRIEF DESCRIPTION OF THE DRAWINGS

The above and other objects, features and other advantages of the present invention will be more apparent from the following detailed description taken in conjunction with the accompanying drawings, in which:

FIGS. 2A through 2F are schematic diagrams, each illustrating a nucleic acid or adsorption medium in the respective steps of the nucleic acid detection method according to an embodiment of the present invention;

FIG. 3 is a schematic diagram of a device for detecting a nucleic acid, according to an embodiment of the present invention.

DETAILED DESCRIPTION OF THE INVENTION

Figure 1:
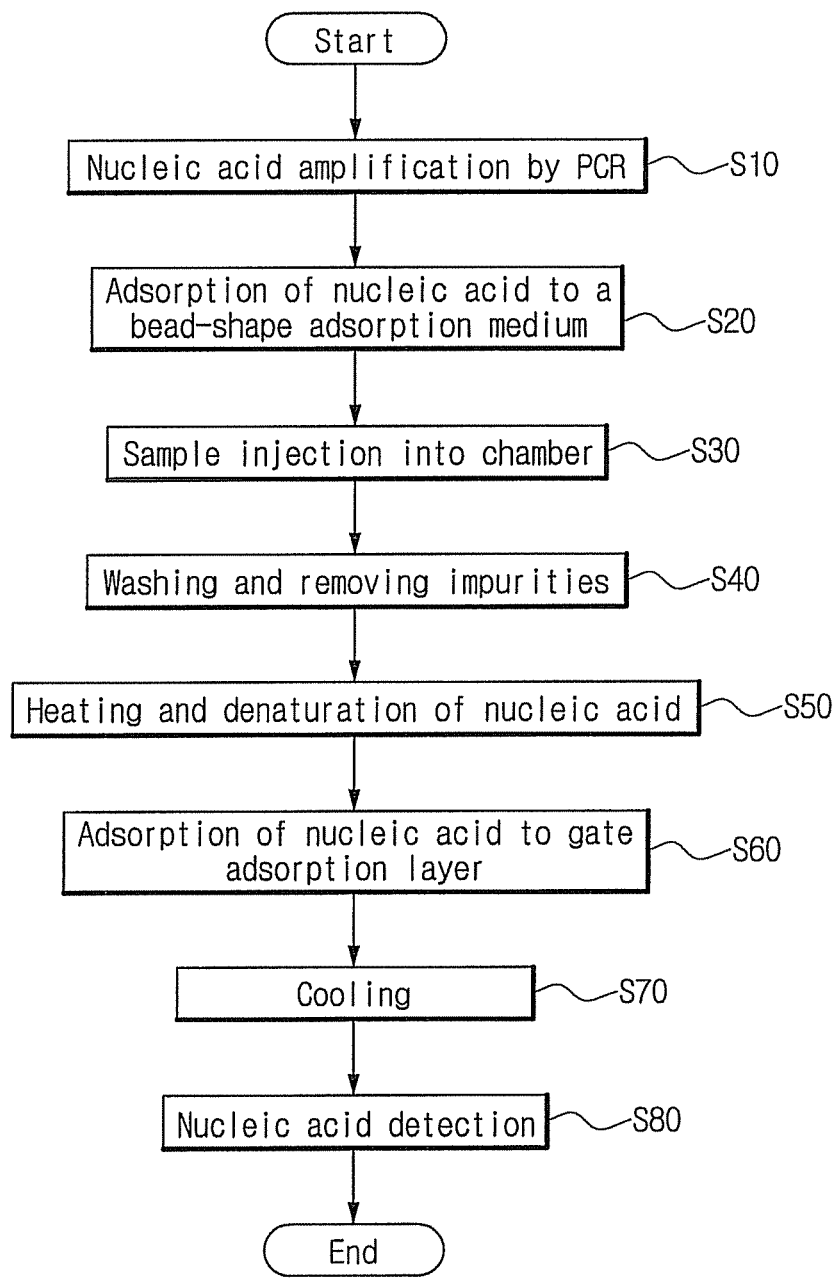
FIG. 1 is a flow chart illustrating a method for detecting a nucleic acid, according to an embodiment of the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Hereinafter, present invention will be set forth in detail with reference to the accompanying drawings.

As used herein, the term "nucleic acid" means DNA, RNA or PNA (peptide nucleic acid), or a combination thereof The DNA, RNA or PNA can be in any possible configuration, i.e., in the form of double stranded (ds) nucleic acid, or in form of single-stranded (ss) nucleic acid, or as a combination thereof (in part ds or ss). In addition, the nucleic acid may be oligo-nucleotide or a polymerase chain reaction ("PCR") product, such as, a refined product of a PCR product. As used herein, the term "biomolecule" means nucleic acid or protein. Exemplary protein molecules include, for example, an enzyme, a substrate, an antigen, an antibody, a ligand, an aptamer, and a receptor.

In one embodiment, the invention provides a method for detecting a gene and a device for detecting a gene. As used herein, the term "gene" means the segment of DNA involved in producing a polypeptide chain; it includes regions preceding and following the coding region (leader and trailer) as well as intervening sequences (introns) between individual coding segments (exons).

FIG. 1 is a flow chart describing a method for detecting a nucleic acid, according to an embodiment of the present invention. FIGS. 2A through 2F are diagrams, each illustrating a gene or adsorption medium in the respective steps of the gene detection method.

In one embodiment, and as illustrated in FIG. 1, the method comprises first amplifying a nucleic acid, such as, for example, a DNA fragment 10 by PCR (S10). In doing so, a sample contains a PCR product is generated. As shown in FIG. 2A, nucleic acid (DNA 10), primers 14 used for PCR amplification, and impurities 16 such as dNTPs, enzyme and salts are present in the sample.

In one embodiment, the primer 14 is labeled with a substance (such as, biotin, amine, an epoxy, carboxylic acid, or thiol) bonded to its end. These substances a capable of forming a crosslink with an adsorption medium, such as beads, allowing for efficient adsorption onto the adsorption medium. For convenience of explanation, as used herein, these labeling substances bonded to the end of the primer will be referred to as a "crosslinking agent".

Next, the PCR product is mixed with an adsorption medium 20 as shown in FIG. 2B, so that the PCR product (DNA 10) among may be adsorbed onto the adsorption medium 20 as shown in FIG. 2C. (S20)

Examples of the adsorption medium 20 include, but are not limited to, beads made of glass, silicon, plastic, gold or magnetic substances.

In addition, adsorption sites 22 may be attached to the surface of the adsorption medium 20 to promote adsorption of the nucleic acid (DNA) 10 (i.e., PCR Product) thereon. For example, substances that can be charged or cause stacking interactions are used for the adsorption site. Examples of such substances include, but are not limited to, streptavidin and polyethyleneimine.

In one embodiment, the sample that includes a bead 18 with adsorbed nucleic acid (DNA) 10 is injected into a chamber 36 of a biomolecule detection device (S30).

Figure 2D:
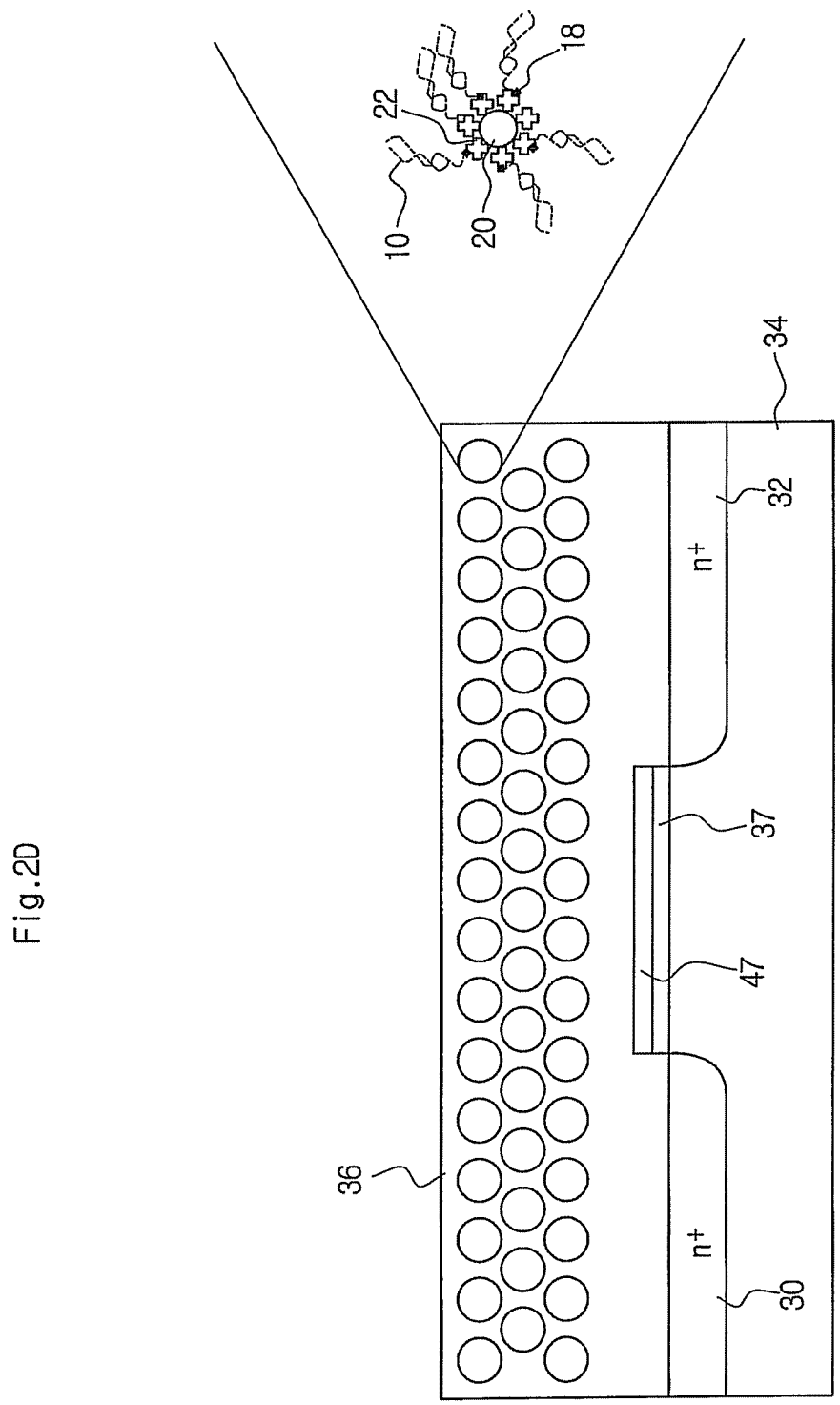

Here, as shown in FIG. 2D, an exemplary embodiment of a biomolecule detection device includes, a source region 30 and a drain region 32 disposed apart from each other on a semiconductor substrate 34; a gate electrode layer 37 formed between the source region 30 and the drain region 32; and a chamber 36 formed over the semiconductor substrate 34 including the gate electrode layer 37, wherein the chamber 36 can be used as a space for accommodating a sample with the nucleic acid (DNA)-absorbed bead 20. In addition, a gate adsorption layer 47 to which a gene is adsorbed is formed on the gate electrode layer 37.

In one embodiment, following adsorption of the gene to the gate adsorption layer 47, the sample in the chamber 36 is then washed with buffer to remove any impurities present in the sample (e.g., dNTPs, enzyme, salts and so on), except for the DNA-absorbed bead 20 (S40).

Thus, according to the present embodiment, the bead 20 with PCR-amplified nucleic acid (DNA 10) adsorbed thereon was first injected into the chamber 36 of the biomolecule detection device (S30) and then impurities were removed by washing (S40). Alternatively, in an alternative embodiment the DNA-adsorbed bead 20 can be washed first to remove impurities (i.e., prior to injecting the sample into the chamber 36 of the biomolecule detection device) in the sample and then injecting the washed bead 20 with adsorbed nucleic acid (DNA 10) into the chamber.

Figure 2E:
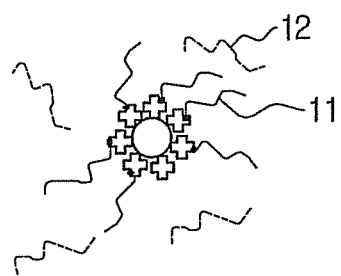

In one embodiment, the sample in the chamber 36 is then heated up to about 90° C. (S50). When the sample temperature is increased to a temperature higher than the nucleic acids melting point (Tm) as in this case, the nucleic acid (DNA 10) in the sample is denatured, so the double-strand structure of the nucleic acid (DNA 10) is converted into single-strand structure as shown in FIG. 2E.

As a result, a single-stranded nucleic acid (DNA 11) having been adsorbed onto the bead 20 is continuously adsorbed, but its complementary single-stranded nucleic acid (DNA12) moves freely in a space (gap) between the beads in the sample and is adsorbed onto the gate adsorption layer 47 formed on the gate electrode layer 37.

Examples of a material of the gate adsorption layer 47 include, but are not limited to, polymers having a positive (+) charge (e.g., polyethyleneimine (PEI), Poly-L-lysine (PLL), etc.) and inorganic materials (e.g., aluminum oxide ($Al_2O_3$), boehmite, etc.). Thus, as shown in FIG. 2F, the single-stranded nucleic acid (DNA 12) with a negative (−) charge on its backbone is adsorbed onto the gate adsorption layer 47.

In one embodiment, the sample is then cooled down (S70) and the biomolecule detection device detects a gene in the sample (S60). That is, when the nucleic acid (DNA in this case) 12 is adsorbed to the gate adsorption layer 47 as shown in FIG. 2F, a channel 35 is formed between the source region 30 and the drain region 32, and current flowing through the channel 35 increases. By measuring the current flowing through the channel between the source region 30 and the drain region 32, the biomolecule detection device is able to verify the presence of a nucleic acid in the sample, and further estimates the amount of nucleic acid.

In one embodiment, the invention provides a device for detecting a nucleic acid, comprising a source region and a drain region disposed apart from each other on a semiconductor substrate; a gate electrode layer formed between the source region and the drain region; a chamber formed over the semiconductor substrate including the gate electrode layer, wherein the chamber can be used as a space for accommodating a gene-containing sample; and a heating means for heating the sample in the chamber, wherein a gate adsorption layer to which a nucleic acid is adsorbed is formed at an upper portion of the gate electrode layer.

In an actual experiment, beads with adsorbed nucleic acid and beads with no adsorbed nucleic acid are loaded into separate chambers, under the same conditions. For both chambers, the currents that flow through the channel between the source region and the drain region are measured and compared with each other.

In one embodiment, the nucleic acid detection device of the present invention has a built-in heating means to more easily heat a sample in the chamber. FIG. 3 is a schematic view of a device for detecting a nucleic acid, according to an embodiment of the present invention, and FIG. 4 is a top view of the device.

Figure 4:
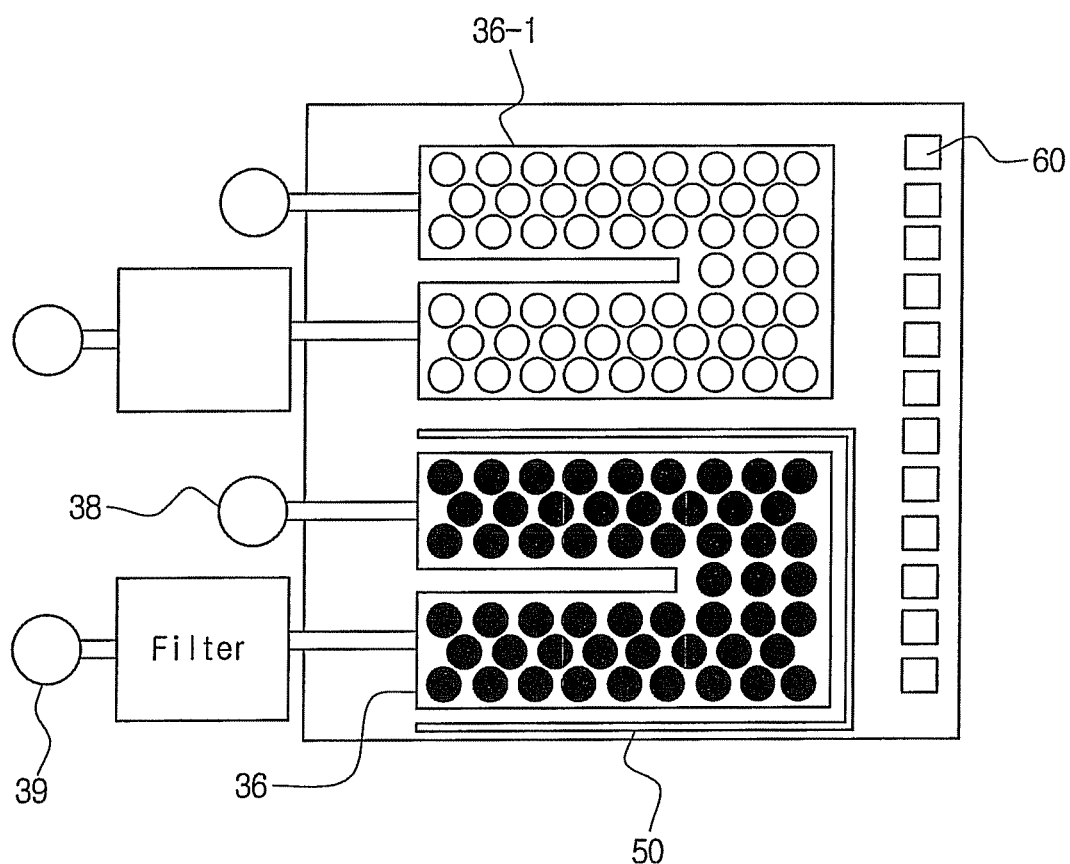
FIG. 4 is schematic diagram illustrating a top view of the device for detecting a nucleic acid, according to an embodiment of the present invention.

As shown in FIGS. 3 and 4, the nucleic acid detection device according to an embodiment of the present invention includes a source region 30 and a drain region 32 disposed apart from each other on a semiconductor substrate 34; a gate electrode layer 37 formed between the source region 30 and the drain region 32; and a chamber 36 formed over the semiconductor substrate 34 including the gate electrode layer 37 to be used as a space for accommodating a sample with the nucleic acid (DNA)-absorbed bead 20. A gate adsorption layer 47 to which a nucleic acid is adsorbed is formed on the gate electrode layer 37. Moreover, a heating means (50 in FIG. 4) for heating the sample in the chamber 36 is built in the device.

Examples of a material of the gate adsorption layer 47 include, but are not limited to, polymers having a positive (+) charge (e.g., PEI, PLL, etc.) and inorganic materials (e.g., aluminum oxide ($Al_2O_3$), boehmite, etc.). Thus, the single-stranded nucleic acid 12 with a negative (−) charge on its backbone is adsorbed onto the gate adsorption layer 47, as shown in FIG. 2F.

In one embodiment, the heating means (50 in FIG. 4) is installed surrounding the chamber 36. For instance, an electric resistor generating heat when power is supplied thereto is employed as the heating means. When power is supplied to the heating means (50 in FIG. 4), heat is generated and the heat is transferred into the chamber 36 through the substrate 34. In FIG. 4, the heating means is installed surrounding the chamber, but it can alternatively be formed on the bottom of the chamber or under the chamber.

In one embodiment, the chamber 36 has a sample inlet 38 for introducing the sample and a sample outlet 39 for discharging the sample. Also, a filter 40 is provided to the outlet 39 so that beads in the sample may not escape to the outside when the sample is injected into the chamber 36.

In another embodiment, the source region 30 and the drain region 32 are provided with electrodes 31 and 33, respectively, to which a voltage is applied. These electrodes 31 and 32 are electrically connected to an electrode pad 60 to receive an externally applied voltage.

To briefly summarize how the nucleic acid detection device works, according to one embodiment, when the sample is put into the chamber 36, a washing operation is carried out to remove impurities produced by the PCR amplification process. Then, the impurity-free sample is heated and the nucleic acid (e.g., DNA) in the sample is denatured. Single-stranded nucleic acids formed by the denaturation are adsorbed to the gate adsorption layer 47. When this occurs, current flowing through the channel 35 between the source region 30 and the drain region 32 is increased. By measuring the current flowing through the channel 35 between the source region 30 and the drain region 32, the device is able to verify the presence of a nucleic acid in the sample, and estimates the amount of the nucleic acid.

Therefore, with the use of an absorption medium for measurement of the nucleic acid amount by PCR, the purification process for removing impurities from the PCR product can be done in much less time.

In an actual experiment, beads with adsorbed nucleic acid and beads with no adsorbed nucleic acid are placed into separate chambers yet under the same environment. For both chambers, currents that flow through the channel between the source region and the drain region are measured and compared with each other.

In one embodiment, the nucleic acid detection device of the present invention preferably includes a control chamber (36-1 in FIG. 4) for accommodating beads with no adsorbed nucleic acid.

While the invention has been shown and described with reference to certain exemplary embodiments thereof, it will be understood by those skilled in the art that various changes in form and details may be made thereto without departing from the spirit and scope of the invention as defined by the appended claims.

In addition, many modifications can be made to adapt a particular situation or material to the teachings of the invention without departing from the essential scope thereof Therefore, it is intended that the invention not be limited to the particular embodiments disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguished one element from another. Furthermore, the use of the terms a, an, etc. do not denote a limitation of quantity, but rather denote the presence of at least one of the referenced item.

What is claimed is:

1. A method for detecting a nucleic acid, comprising:
providing a field-effect transistor (FET) based biomolecule detection device comprising:
a source region and a drain region disposed apart from each other on a semiconductor substrate,
a gate electrode layer formed between the source region and the drain region,
a gate adsorption layer formed on an upper surface of the gate electrode layer, wherein the gate adsorption layer comprises a polymer having a positive (+) charge or an inorganic material,
a chamber formed over the semiconductor substrate including the gate electrode layer, wherein the chamber can be used as a space for accommodating the nucleic acid-containing sample;
injecting a sample containing an adsorption medium with a nucleic acid adsorbed thereon into the chamber of the biomolecule detection device;
washing the sample in the chamber to remove impurities;
heating the sample in the chamber to denature the nucleic acid, wherein the heat is generated by a heating means within the semiconductor substrate;
adsorbing the denatured nucleic acid to the gate adsorption layer of the biomolecule detection device;
cooling down the sample; and
detecting a nucleic acid in the sample by using the biomolecule detection device.

2. The method according to claim 1, further comprising the step of adsorbing the nucleic acid onto the adsorption medium before injecting the sample containing the adsorption medium with the nucleic acid adsorbed thereon into the chamber of the biomolecule detection device.

3. The method according to claim 1, wherein a crosslinking agent is bonded to an end of the nucleic acid as a labeling substance of a primer in a nucleic acid amplification process.

4. The method according to claim 1, wherein an adsorption site for the nucleic acid is provided on the surface of the adsorption medium.

5. The method according to claim 4, wherein the adsorption site comprises a chargeable substance or a substance causing stacking interactions.

6. The method according to claim 4, wherein the adsorption site comprises streptavidin or polyethyleneimine.

7. The method according to claim 1, wherein the adsorption medium is in form of a bead made of a material that is selected from the group consisting of glass, silicon, plastic, gold and magnetic substances.

8. A method for detecting a nucleic acid, comprising:
washing a sample containing an adsorption medium with a nucleic acid adsorbed thereon to remove impurities;
providing a field-effect transistor (FET) based biomolecule detection device comprising:
a source region and a drain region disposed apart from each other on a semiconductor substrate,
a gate electrode layer formed between the source region and the drain region,
a gate adsorption layer formed on an upper surface of the gate electrode layer, wherein the gate adsorption layer comprises a polymer having a positive (+) charge or an inorganic material,
a chamber formed over the semiconductor substrate including the gate electrode layer, wherein the chamber can be used as a space for accommodating the nucleic acid-containing sample;
injecting the washed sample into a chamber of the field-effect transistor (FET) based biomolecule detection device;
heating the sample in the chamber to denature the nucleic acid, wherein the heat is generated by a heating means within the semiconductor substrate;
adsorbing the denatured nucleic acid to the gate adsorption layer of the biomolecule detection device;
cooling down the sample; and
detecting a nucleic acid in the sample by using the biomolecule detection device.

9. The method according to claim 8, further comprising the step of adsorbing the nucleic acid onto the adsorption medium before washing the sample containing the adsorption medium with the nucleic acid adsorbed thereon.

10. The method according to claim 8, wherein a crosslinking agent is bonded to an end of the nucleic acid as a labeling substance of a primer in a gene amplification process.

11. The method according to claim 8, wherein an adsorption site for the nucleic acid is provided on the surface of the adsorption medium.

12. The method according to claim 11, wherein the adsorption site is a chargeable substance or a substance causing stacking interactions.

13. The method according to claim 11, wherein the adsorption site comprises streptavidin or polyethyleneimine.

14. The method according to claim 8, wherein the adsorption medium is in form of a bead made of a material that is selected from the group consisting of glass, silicon, plastic, gold and magnetic substances.

* * * * *